United States Patent
Weaver

(10) Patent No.: US 10,039,696 B2
(45) Date of Patent: *Aug. 7, 2018

(54) HIGHLY PROTONATED HYDRONIUM AND PEROXYMONOSULFURIC ACID AS A SANITIZING SOLUTION

(71) Applicant: APHEX BIOCLEANSE SYSTEMS, INC., Pittsford, NY (US)

(72) Inventor: David J. Weaver, Rochester, NY (US)

(73) Assignee: Aphex BioCleanse Systems, Inc., Pittsford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,000

(22) Filed: Jan. 6, 2017

(65) Prior Publication Data
US 2017/0119635 A1    May 4, 2017

Related U.S. Application Data

(63) Continuation-in-part of application No. 14/926,148, filed on Oct. 29, 2015, now abandoned.

(51) Int. Cl.

| | | |
|---|---|---|
| A01N 47/28 | (2006.01) |
| A61K 31/17 | (2006.01) |
| A61K 8/23 | (2006.01) |
| A61K 8/41 | (2006.01) |
| A61K 8/42 | (2006.01) |
| A61K 8/73 | (2006.01) |
| A61Q 17/00 | (2006.01) |
| A61K 8/22 | (2006.01) |
| A61K 45/06 | (2006.01) |
| A61L 2/00 | (2006.01) |
| A61K 31/14 | (2006.01) |
| A61L 2/18 | (2006.01) |
| A01N 59/00 | (2006.01) |
| A61K 9/00 | (2006.01) |
| A61K 9/06 | (2006.01) |
| A61K 47/36 | (2006.01) |

(52) U.S. Cl.
CPC ........... *A61K 8/23* (2013.01); *A01N 59/00* (2013.01); *A61K 8/22* (2013.01); *A61K 8/416* (2013.01); *A61K 8/42* (2013.01); *A61K 8/73* (2013.01); *A61K 31/14* (2013.01); *A61K 31/17* (2013.01); *A61K 45/06* (2013.01); *A61L 2/00* (2013.01); *A61L 2/186* (2013.01); *A61Q 17/005* (2013.01); *A61K 9/0014* (2013.01); *A61K 9/06* (2013.01); *A61K 47/36* (2013.01)

(58) Field of Classification Search
CPC . A61K 8/22; A61K 8/23; A61K 8/416; A61K 8/42; A61K 8/73; A61Q 17/005
See application file for complete search history.

(56) References Cited

U.S. PATENT DOCUMENTS

| | | | | |
|---|---|---|---|---|
| 4,534,945 A * | 8/1985 | Hopkins | ............... | C01B 15/037 |
| | | | | 423/272 |
| 2002/0168423 A1* | 11/2002 | Wurzburger | ........... | A61K 33/06 |
| | | | | 424/709 |
| 2008/0253976 A1* | 10/2008 | Scott | ..................... | A61K 8/0216 |
| | | | | 424/49 |

FOREIGN PATENT DOCUMENTS

| | | | | |
|---|---|---|---|---|
| JP | 2012012654 A * | 1/2012 | | |
| WO | WO 9108981 A2 * | 6/1991 | ............. | A01N 59/00 |

* cited by examiner

*Primary Examiner* — Jean P Cornet
(74) *Attorney, Agent, or Firm* — Woods Oviatt Gilman LLP; Dennis B. Danella, Esq.

(57) ABSTRACT

A water-based, alcohol-free, skin and hard surfaces sanitizing solution with a natural skin softener, where the nature of the biocidal enhancer used in the process of making the solution significantly increases efficacy while simultaneously enabling much more economical manufacturing, processing and transportation of the product. As the present solution is water-based, no further moisturizing additives are required, and those with sensitive skin, diabetes, allergies or religious beliefs are able to use the product without concern.

3 Claims, No Drawings

HIGHLY PROTONATED HYDRONIUM AND PEROXYMONOSULFURIC ACID AS A SANITIZING SOLUTION

PRIORITY CLAIM AND RELATED APPLICATIONS

This continuation-in-part application claims the benefit of priority from application U.S. Ser. No. 14/926,148 filed Oct. 29, 2015. Said application is incorporated by reference in its entirety.

FIELD OF THE INVENTION

In one aspect, the invention relates to a solution including hydronium, sulfuric acid and hydrogen peroxide effective as a biocide applicable to both skin and hard surfaces.

In one aspect, the invention relates to an unsubstituted quaternary ammonium salt that is an effective biocide in combination with a germicidal/bactericidal ingredient, alkyl-dimethyl-benzyl-ammonium chloride (Benzalkronium Chloride or BAC) and carbamide peroxide ($CH_6N_2O_3$).

In one aspect, the invention describes a desirable effect of the chemistry combination where the creation of hydronium ions are known to mediate chemical reactions by attaching themselves to the hydrophilic ends of molecules, specifically sites with partial negative charges or rich in electron density. The formation of an adduct, for steric hindrance where adding carbamide to the existing molecular chain will form a lightly bonded bi-molecule chain making the quaternary ammonia salt larger and more difficult to penetrate the skin flora while maintaining its germicidal functionality. The described unsubstituted quaternary ammonium salt composition with other ingredients has been shown to be effective in testing against *E-coli, Salmonella, Pseudomonas, Listeria,* H1N1, NDM1, *Clostridium Difficile* or c-*Difficile* spores, Rhinovirus, MRSA and a wide range of other bacteria and viruses, molds and spores.

Other additives such as scents, humectants, antifungal, anti-inflammatory, cicatrizants and hemostatic agents can be added to the chemistry combination to promote healing as well as other medicinal benefits.

BACKGROUND OF THE INVENTION

Hand sanitizers have been marketed and sold for decades. However, nearly all sanitizers use alcohol at a minimum of 62% concentration as both an antiseptic and a drying agent. According to Center for Disease Control (CDC) recommendations, a hand sanitizer should contain at least 60% alcohol by volume in order to be effective. Alcohol is harsh on the skin, and also is not recommended for use by people with diabetes as it can dramatically affect blood glucose readings. Certain religious beliefs restrict the use of alcohol on the hands and providing a non-alcohol-based hand sanitizer with effective killing rates addresses problem for a large community.

Alcohol-free hand sanitizers are available, but their effectiveness is limited by the number of active ingredients allowed under the FDA 1974 Tentative Final Monograph. Thus, it is necessary to find an ingredient, or combination of ingredients, that can significantly enhance the allowed biocides from the Monograph.

The FDA requirement for hand sanitizers must include active ingredient from a list identified in the FDA 1978 Monograph. One specific biocide listed in the Monograph is Benzalkronium Chloride (BAC) that acts as a sanitizer to disrupt the cellular membrane of micro-organisms. The biocide activity of BAC is enhanced by the action of the long chain substitutes, acting as solvents of the lipid (or other soluble) parts of the cellular membrane. This event disrupts the integrity of the cellular membrane causing the outflow of the intracellular liquid. The addition of a mineral acid as $H_2SO_4$ lowers the pH of the system, leading to the formation of hydronium ions.

Hydronium ions are known to mediate chemical reactions by attaching themselves to the hydrophilic ends of molecules, specifically sites with partial negative charges or rich in electron density. H+ will bond disrupting the general characteristics of the lipid while the long chain of BAC will solvate the hydrocarbon chain.

In addition, the solution may contain other ingredients not listed as active by the FDA and may include but not limited to natural moisturizers such as carbamide. The described unsubstituted quaternary ammonium salt composition is compatible with different aromas and fragrances, such as Rose Water, Witch Hazel, Lavender, Lilac and is not limited by one or more volatilized chemical compounds that can be added to the solution at a very low concentration that stimulates the human olfactory senses.

Carbamide is also highly water-soluble due to its ability to form multiple hydrogen bonds with the low pH hydronium ions in the chemistry composition. The natural conditioning properties of carbamide, also called urea peroxide, urea hydrogen peroxide (UHP), and percarbamide, is an adduct of hydrogen peroxide and urea and is similar to hydrogen peroxide as an oxidizer. Carbamide has several other applications. In veterinary medicine, for instance, it is used as a topical antiseptic and a diuretic.

Carbamide appears as a white crystalline solid which dissolves in water to give free hydrogen peroxide and is readily available with the solubility of commercial samples varying from 0.05 g/ml to more than 0.6 g/ml. The chemical formula is $CH_6N_2O_3$. As a natural skin conditioner the allergic reactions by users to dyes and chemicals found in readily available alcohol-based hand sanitizers is avoided. The use of low doses of Carbamide has shown to reduce the effects of acne and psoriasis on the skin without damaging side effects found in some medications. The Applicant further discovered that a mixture of carbamide and hydronium aids in creating amino acids that are the building blocks for proteins to promote healing in wound beds. These proteins create an immune system that identifies and neutralizes pathogens such as bacteria and viruses. In one embodiment, carbamide is supplied in the amount of from about 0.004% to about 4% by weight of the total weight of the skin sanitizing and wound healing solution. In some instances, carbamide is better known as urea ($CH_4N_2O$). Carbamide reacts with the organic acid in the present protonated solution and creates uronium hydrogen sulfate ($CH_4N_2O.H_2O_4S$). This solution differs from urea hydrogen peroxide (UHP or $CO(NH_2)_2.H_2O_2$) found in tooth paste. Uronium Hydrogen Sulfate promotes rehydration of the skin and wound healing along with the water in the solution. In wound healing, the key elements of an amino acid are carbon, hydrogen, oxygen, and nitrogen. These are created by a chemical chain of $CH_4N_2O.H_2O_4S$ in the solution though other elements are found in the side-chains of certain amino acids.

As documented in Wikipedia website, Aloe vera is now widely used on facial tissues, where it is promoted as a moisturizer and/or anti-irritant to reduce chafing of the nose of users suffering hay-fever or cold. Aloe vera is also used for soothing the skin, and keeping the skin moist to help avoid flaky scalp and skin in harsh and dry weather. Aloe vera may also be used as a moisturizer for oily skin. Aloe vera can be easily added to the described highly protonated, low pH, nondermathropic solution as a moisturizer. Taspine is an alkaloid extracted from trees of Croton (family Euphorbiaceae) of the western Amazon region that has been used by natives and others as a vulnerary agent when purified from the tree sap. Some testing and data suggest that taspine promotes early phases of wound healing in a dose-dependent manner with no substantial modification thereafter. Its mechanism of action is probably related to its chemotactic properties on fibroblasts and is not mediated by changes in extracellular matrix. Additionally, Taspine can be added to the described highly protonated, low pH, nondermathropic solution as a natural moisturizer and wound healing ingredient.

SUMMARY OF THE INVENTION

The described invention of using a base chemistry where a high concentration of Hydronium Ions is created as a base chemistry where other ingredients described in the invention forms a composition that both reduces bacteria on the skin and a natural moisturizer with extended protection up to forty-eight hours after application to the skin. As a result, the described skin sanitizing solution both sanitizes and moisturizes the skin on contact without the addition of harsh chemicals, such as alcohol, and without the need for skin conditioning additives that may contain objectionable chemistry, dyes and perfumes.

DETAILED DESCRIPTION OF THE INVENTION

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

In one aspect, the invention is an unsubstituted quaternary ammonium salt composition with other ingredients that comprises a composition that is non-flammable, alcohol-free, non-stinging, highly protonated, and nondermatropic. The composition has a very high hydronium proton count and is created by a process involving the blending of a premix that comprises a highly protonated, non-corrosive, nondermatropic hydronium carrier and a biocide, added to a predetermined quantity of water until it dissolves. In one embodiment, the present hydronium comprises a proton count of between about $4\times10^{20}$ and about $5.8\times10^{23}$. In one embodiment, the present hydronium disposed at a pH of from about 1.5 to about 1.8 is found suitable for hand sanitizing or any applications requiring contact with human skin while the preferable pH range for hard surface sanitizing or any applications where contact with human skin is not a concern, ranges from about 0.5 to about 1.2. In one embodiment, the biocide further comprises one or more quaternary ammonium compounds.

The described unsubstituted quaternary ammonium salt composition with other ingredients comprises a blend of an inorganic acid, a sulfate, and water or a blend of organic acid, a sulfate, and water. The quaternary ammonium compound is selected from one or more of the group consisting of Benzalkonium Chloride, Cetylpyridinium Chloride, Silver Chloride adsorbed to titanium dioxide (initially notified under silver chloride), Cetalkonium chloride, Benzyldimethyl (octadecyl) ammonium chloride, Miristalkonium chloride, Dimethyldioctylammonium chloride, Hydrogen chloride/hydrocholoric acid, Silver Chloride, Dodecylguanidine monohydrochloride, Bromine chloride, Dimethyloctadecyl [3-(trimethoxysilyl) propyl] ammonium chloride, Decyldimethyloctylammonium chloride, Benzyldimethyloleylammonium chloride, Dimethyltetradecyl[3-(trimethoxysilyl)propyl]ammonium chloride, benzylcoco alkyldimethyl chlorides, dicocoalkyl dimethyl, chlorides, bis (hydrogenated tallow alkyl) dimethyl chlorides, benzyl-c8-18-alkyldimethyl chlorides, benzyl-c12-18-alkyldimethyl chlorides, di-C6-12-alkyldimethyl chlorides, benzyl-c8-16-alkyldimethyl chlorides, di-c8-10-alkyldimethyl chlorides, benzyl-C10-16-alkyldimethyl chlorides, Octenidine dihydrochloride di-C8-18 alkyldimethyl, chlorides, benzyl-C12-14-alkyldimethyl chlorides, C12-14-alkyl[(ethylphenyl) methyl]dimethyl chlorides.

The inorganic acid is selected from one or more of the group consisting of sulfuric acid, hydrochloric acid, nitric acid, phosphoric acid, boric acid, hydrofluoric acid, hydrobromic acid.

The organic acid selected from one or more of the group consisting of lactic acid, acetic acid, formic acid, citric acid, oxalic acid, uric acid.

The solution may further comprise a skin permeation enhancer or conditioner selected from one or more of the group consisting of natural components and vitamins, minerals, urea or anti-oxidants to enhance the composition's natural skin moisturizing and protection against the spread of acne and psoriasis.

A thickener may be added to make a gel formula solution. The thickener is selected from one or more of the group consisting of Xanthan gum, Alginic acid, Sodium alginate, Ammonium alginate, Calcium alginate, Propylene glycol alginate, Propane-1,2-diol alginate, Agar, Carrageenan, Processed euchuema seaweed, Furcelleran, Aribinogalactan larch gum, Locust Bean (carob gum), Oat gum, Guar gum, Tragacanth, Acadia Gum (Gum Arabic), Karaya gum, Tara Gum, Gellan gum, Sorbitol, Mannitol, Glycerol, Konjac, Konjac gum, Polyoxyethylene (8) sterate, Polyoxyl 8 stearate, Polyoxyethylene (40) stearate, Polyoxyethylene (20) sorbitan monolaurate (polysorbate 20), Polysorbate 80, Polyoxethylene sorbitan mono-oleate, Polyoxethylene sorbitan monopalminate, Polysorbate 40, Tween 40, Polyexthylene sorbitan monostearate, Polysorbate 60, Tween 60, Polyoxyethylene-20-sorbitan tristearate, Polysorbate 65, Tween 65, Pectin, Amidated pectin, Gelatine, Ammonium phosphatides, Sucrose acetate isobutyrate, SAIB, Sucrose diacetate hexaisobutyrate, Glycerol esters of wood rosins, Sodium and potassium pyrophosphates, Diphosphates, Ammonium phosphate (diabasic and monobasic), Sodium and potassium triphosphate, Triphosphate, Sodium and potassium polyphosphates, Polyphosphates, Beta-cyclodextrine, Cellulose (microcrystalline and powdered), Methyl cellulose, Ethyl cellulose, Hydroxypropyl cellulose, Hydroxypropyl methyl cellulose, Methylethylcellulose, Carboxymethyl cellulose, Sodium carboxymethyl cellulose, Crosslinked sodium carboxymethyl cellulose, Sodium caseinate, Magnesium stearate, Sodium, potassium and calcium salts of fatty acids, Magnesium salts of fatty acids, Mono- and diglycerides of fatty acids (glyceryl monostearate, glyceryl distearate), Acetic and fatty acid esters of glycerol, Acetic acid esters of mono- and diglycerides of fatty acids, Lactic and fatty acid esters of glycerol, Lactic acid esters of mono- and diglycerides of fatty acids, Citric and fatty acid esters of glycerol, Citric acid esters of mono- and diglycerides of fatty acids, Tartaric and fatty acid esters of glycerol, Tartaric acid esters of mono- and diglycerides of fatty acids, Diacetyltartaric and fatty acid esters of glycerol, mon- and diacetyl tartaric acid esters of monoand diglycerides of fatty acids, Mixed acetic and tartaric acid esters of mono- and diglycerides of fatty acids, Sucrose esters of fatty acids, Sucroglycerides, Polyglycerol esters of fatty acids, Polyglycerol esters of interesterified ricinoliec acid, Propylene glycol mono- and di-esters, Propane 1,2-Diol esters of fatty acids, Lactylated fatty acid esters of glycerol and propane-1,2-diol, Thermally oxidized soy bean oil interacted with mono- and diglycerides of fatty acids, Dioctyl sodium sulphosuccinate, Sodium oleyl or stearoyl lactylate stearoyl-2-lactylate, Calcium stearoyl-2-lactylate, Stearyl tartrate, sorbitan monostearate, Sorbitan tristearate, Span 65, Sorbitan monolaurate, Span 20, Sorbitan mono-oleate, Span 80, Sorbitan monopalmitate, Span 40.

The unsubstituted quaternary ammonium salt created by the invention was tested by an independent laboratory and the results recorded for each microbe studied. It is important to note that alcohol-based hand sanitizers with or without the active ingredient BZK does not offer the same results against MRSA, c-*Difficile* spores, H1N1.

| Microbe | | Untreated Control | Average Number Recovered | Percent Reduction |
|---|---|---|---|---|
| MRSA (30 Seconds) | | $1.7 \times 10^5$ | $3.3 \times 10^0$ | 99.998% |
| MRSA (180 Seconds) | | $1.7 \times 10^5$ | $<1.0 \times 10^0$ | 99.999% |
| c-*Difficile* | Trial 1 | $3.3 \times 10^3$ | <1.00 | 99.97% |
| spores | Trial 2 | $3.3 \times 10^3$ | <1.00 | 99.97% |
| | Trial 3 | $3.3 \times 10^3$ | <1.00 | 99.97% |
| | Trial 4 | $3.3 \times 10^3$ | <1.00 | 99.97% |
| | Trial 5 | $3.3 \times 10^3$ | <1.00 | 99.97% |
| NDM-1 | Trial 1 | $9.6 \times 10^5$ | <5.0 | 99.9995% |
| | Trial 2 | $9.6 \times 10^5$ | <5.0 | 99.9995% |
| | Trial 3 | $9.6 \times 10^5$ | <5.0 | 99.9995% |
| | Trial 4 | $9.6 \times 10^5$ | <5.0 | 99.9995% |
| | Trial 5 | $9.6 \times 10^5$ | <5.0 | 99.9995% |
| Rhinovirus 39 | | $6.7 \times 10^5$ | $4.8 \times 10^0$ | 99.993% |
| *Influenza A* (H1N1) | | $3.1 \times 10^4$ | <2.2 | 99.993% |
| PRD-1 Bacteriophage | | $2.0 \times 10^4$ | $4.3 \times 10^0$ | 99.98% |
| *E. Coli* | | $9.10 \times 10^5$ | <0.5 | 99.9999% |
| *E. Coli* (Dry Test) | | $5.6 \times 10^4$ | $3.7 \times 10^2$ | 99.3% |
| *Salmonella Enterica* | | $1.1 \times 10^6$ | <0.5 | 99.9999% |
| *Salmonella Enterica* (Dry Test) | | $1.6 \times 10^5$ | $1.6 \times 10^2$ | 99.9% |

This product is manufactured according to FDA Tentative Final Monograph (1974, 1978, 1991, 1994, 2002). All testing is performed by an independent registered laboratory, according to test methods described in AOAC Official Method 961.02 (Germicidal Spray Products as Disinfectants), ASTME 1053-97 (Standard Test Method for Efficacy of Virucidal Agents Intended for Inanimate Surfaces), and from ASTM E2111-00 (Standard Quantitative Carrier Test Method to Evaluate the Bactericidal, Fungicidal, Mycobactericidal and Sporicidal Potencies of Liquid Chemical Germicides). The FDA does not specify testing protocols for this product. Copies of full reports are available upon request.

The solution also was graded minimally irritating at 2.8 (non-irritant) on the standardized Draize Test scale where 0 is non-irritating and 110 is severe/extreme where skin damage will occur.

According to Wikipedia website, the Draize Test is an acute toxicity test devised in 1944 by the Food and Drug administration (FDA) toxologists John H. Draize and Jacob M. Spines. Initially used for testing cosmetics, the procedure involves applying 0.5 mL or 0.5 g of a test substance to the eye or skin of a restrained, conscious animal, and then leaving it for set amount of time before rinsing it out and recording its effects. The animals are observed for up to 14 days for signs of erythema and edema in the skin test, and redness, swelling, discharge, ulceration, hemorrhaging, cloudiness, or blindness in the tested eye. The test subject is commonly an albino rabbit, though other species are used too, including dogs. The animals are euthanized after testing if the test renders irreversible damage to the eye or skin. Animals may be re-used for testing purposes if the product tested causes no permanent damage. Animals are typically reused after a "wash out" period during which all traces of the tested product are allowed to disperse from the test site. The FDA supports the test, stating that "to date, no single test, or battery of tests, has been accepted by the scientific community as a replacement [for] . . . the Draize test"

Preferred Embodiment

In one embodiment, the invention includes the use of the described unsubstituted quaternary ammonium salt composition with other ingredients which are fully incorporated herein by reference, as the Ionic Carrier premix. In this embodiment, 10 grams of the described highly protonated, low pH, nondermathropic solution are blended in a 1:2 ratio with water, by weight. This blend is then added to 5.5 grams of Benzalkonium Chloride, mixed with 3 grams of Urea, and 481.5 grams of water.

The amount of thickener can vary, depending upon the final intended use. 0.5% to 1% xanthan gum gives a good consistency for a hand gel. The formula is a composition, which is a highly protonated, supercharged, non-corrosive liquid proton suspending composition.

The manufacturing process to create the described unsubstituted quaternary ammonium salt with is well known and beginning as early as the 1980's various chemists and inventors have experimented with the nature of this reaction of adding acid to the water. Generally speaking, these reactions and resulting compounds have lacked stability and the manufacturing process was extremely expensive for commercialization. However, this invention has created a compound reaction of the several elements for making the described unsubstituted quaternary ammonium salt composition with other ingredients of adding sulfuric acid of at least 88% purity in a controlled manner to water while vigorously stirring and agitating said solution to control the temperature of the exothermic reaction.

In one embodiment, another sanitizing solution suitable for sanitizing both skin and hard surface is provided. As used herein, a hard surface is defined as an inanimate, non-porous surface, e.g., but not limited to, stainless steel, glass, aluminum, epoxy, enamel, acrylic, Mipolam®, vinyl, hardwood, melamine covered wood, plastic, Plexiglas®, chromium, kitchen surfaces, bathroom surfaces, tub surfaces and tile surfaces. In producing this solution, a base solution of hydronium having a proton count between about $4 \times 10^{20}$ and about $5.8 \times 10^{23}$ is first provided. This solution is then mixed with an inorganic acid, e.g., sulfuric acid ($H_2SO_4$), hydrogen peroxide ($H_2O_2$) and water to yield peroxymonosulfuric acid ($H_2SO_5$) and hydronium. In one embodiment, a 35% active hydrogen peroxide ($H_2O_2$) is added to the base solution in a (equilibrium) reaction stoichiometry at 1:1. For example, a solution containing 0.181 grams of sulfuric acid ($H_2SO_4$) will require 0.0628 grams or 1/35 grams of hydrogen peroxide ($H_2O_2$) to produce peroxymonosulfuric acid at a pH of 0.7. The balanced chemical equation for the reaction between sulfuric acid and hydrogen peroxide can be written as:

$$H_2SO_4\,(aq) + H_2O_2\,(aq) \underset{}{\overset{K_{eq}}{\rightleftharpoons}} H_2SO_5\,(aq) + H_2O\,(l)$$

Under the condition of constant volume and using the obtained first-order forward and reverse rate constants $k_f$ and $k_r$, the value of $K_{eq}$ at 298 K is about $2.4\times10^5$. As a result, the formation of peroxymonosulfuric acid ($H_2SO_5$(aq)) is highly favored under typical ambient conditions from mixtures of aqueous solutions of sulfuric acid and hydrogen peroxide. In one embodiment, additional sulfuric acid is added to provide unreacted sulfuric acid to enhance the efficacy of the mixture in certain applications. Other suitable inorganic acids include, but not limited to hydrochloric acid, nitric acid, phosphoric acid, boric acid, hydrofluoric acid and hydrobromic acid. Due to its very high reactivity the standard reduction potential of peroxymonosulfuric acid is difficult to measure. The potassium salt of this peracid is known to have a reduction potential of +1.85 Volts vs. the standard hydrogen electrode, placing it higher in reduction potential than most aqueous oxidants. It is likely that aqueous solutions of the free peracid would at least transiently possess even higher standard reductions potentials. A thickener, as disclosed elsewhere herein, can also be applied to this embodiment to facilitate its application to skin or hard surfaces.

Several tests were carried out to examine the efficacies of the present solution on skin and a hard surface. The resultant solution including peroxymonosulfuric acid is observed to attacks germ cells (including c-*Difficile* spores) without damaging the skin and integrity of the surface or equipment. In preparing for tests on hard surface, c-*Difficile* spores production and purification were performed according to EPA SOP MB-28-04: Production of c-*Difficile* spores for use in the efficacy evaluation of antimicrobial agents. The method was based on ASTM Standard E2839-11 for producing standardized spore suspensions of c-*Difficile*. Tests were carried out according to EPA SOP MB-31-03. This quantitative method is used to assess the sporicidal efficacy of disinfectants against c-*Difficile* spores (ATCC 43598) on inanimate, hard and non-porous surfaces. Each soiled sample of 5% Tripartite was treated with the present resultant solution including peroxymonosulfuric acid and observed after a period of treatment to show its efficacy against c-*Difficile* spores.

It should be understood that the preceding is merely a detailed description of one or more embodiments of this invention and that numerous changes to the disclosed embodiments can be made in accordance with the disclosure herein without departing from the spirit and scope of the invention. The preceding description, therefore, is not meant to limit the scope of the invention. Rather, the scope of the invention is to be determined only by the appended claims and their equivalents.

What is claimed herein is:

1. A sanitizing solution consisting of hydronium having a proton count between $4\times10^{20}$ and $5.8\times10^{23}$, sulfuric acid, hydrogen peroxide and water.

2. The sanitizing solution according to claim 1, wherein the hydrogen peroxide is about 35% by weight of the weight of said sulfuric acid and water.

3. A sanitizing solution consisting of hydronium having a proton count between $4\times10^{20}$ and $5.8\times10^{23}$, sulfuric acid, hydrogen peroxide, xanthan gum and water.

\* \* \* \* \*